United States Patent [19]

Adams et al.

[11] Patent Number: 4,945,775
[45] Date of Patent: Aug. 7, 1990

[54] INERTIAL BASED PIPELINE MONITORING SYSTEM

[75] Inventors: John R. Adams; Patrick S. Price; Jim W. Smith, all of Calgary, Canada

[73] Assignee: Pulsearch Consolidated Technology Ltd., Calgary, Canada

[21] Appl. No.: 362,504

[22] Filed: Jun. 7, 1989

[30] Foreign Application Priority Data

Dec. 30, 1988 [CA] Canada .................................. 587332

[51] Int. Cl.⁵ .............................................. G01C 9/06
[52] U.S. Cl. .................................................... 73/865.8
[58] Field of Search ................... 73/623, 865.8, 866.5, 73/865.9

[56] References Cited

U.S. PATENT DOCUMENTS

| | | | |
|---|---|---|---|
| 2,940,302 | 4/1956 | Scherbatskoy | 73/40.5 |
| 3,495,546 | 2/1970 | Brown et al. | 73/866.5 |
| 3,786,684 | 1/1974 | Wiers et al. | 73/432 |
| 3,810,384 | 5/1974 | Evans | 73/623 |
| 3,960,006 | 6/1976 | Smith | 73/67.8 |
| 4,052,686 | 10/1977 | Schmitz | 336/65 |
| 4,162,635 | 7/1979 | Triplett et al. | 73/623 |
| 4,598,585 | 7/1986 | Boxenhorn | 73/517 R |
| 4,641,529 | 2/1987 | Lorenzi et al. | 73/623 |
| 4,655,085 | 4/1987 | Tomizawa et al. | 73/638 |
| 4,665,734 | 5/1987 | Joet | 73/622 |
| 4,744,246 | 5/1988 | Busta | 73/204.26 |
| 4,747,317 | 5/1988 | Lara | 73/865.8 |
| 4,756,229 | 7/1988 | Drakeley | 73/1 D |
| 4,757,716 | 7/1988 | Nottingham et al. | 73/623 |

*Primary Examiner*—Robert Raevis
*Attorney, Agent, or Firm*—Merchant, Gould, Smith, Edell, Welter & Schmidt

[57] ABSTRACT

A pipeline monitoring system for determining profile, ovality and displacement of oil, gas and products pipelines. The system comprises one or more pig carriers housing a plurality of sensors including a strapdown inertial measurement system, a secondary sonar measurement system, digital recorder, weld detector and odometer. The inertial measurement system detects primary acceleration and orientation data of the monitoring system within a pipeline and the secondary system generates redundant data for verifying the acceleration orientation information provided by the inertial system. The digital recorder records all of the information generated by the various measurement systems and sensors for post ash processing analysis to determine the aforementioned features of profile, ovality and displacement of pipelines.

20 Claims, 7 Drawing Sheets

INERTIAL BASED PIPELINE MONITORING SYSTEM

SUMMARY OF THE INVENTION

The present invention relates to pipeline monitoring systems, and more particularly to an inertial pipeline pig housing primary sensors and secondary redundant sensors for determining profile, ovality and displacement of oil, gas and products pipelines.

Deformation monitoring of all pipelines is essential to forecasting integrity changes which allow corrective measures to be taken before actual pipeline failure occurs. Independent studies indicate that there are currently approximately 423,000 kilometers of pipelines in North America which are subject to such integrity changes as a result of frost, subterranean earth movement, etc.

Previous attempts to build inertial pigs and even inertial survey systems have relied upon sophisticated software operating in real time to compute the initial survey data and to control onboard sensor systems. Raw data from the sensor systems is then processed into an intermediate form which is recorded. In the event that errors are introduced into the processing, it is impossible in such prior art systems to recover from these errors via post-processing since the raw data is no longer available.

Various other prior art pipeline pigs have relied on mechanical components to measure such characteristics as location, curvature, and ovality.

For example, Canadian Pat. No. 1,083,343 (Pallan) teaches a pipeline pig having a plurality of wheels mounted on the body portion thereof for engagement with the wall of a pipeline. The wheels operate in conjunction with hydraulic displacement apparatus for controlling speed of the pig within the pipeline.

Canadian Pat. No. 1,107,494 (Institut Francais du Petrole France) teaches the use of a mechanical arm oriented in parallel with the axis of the pipeline and urged into contact therewith for detecting the diameter of the pipeline.

Canadian Pat. No. 1,019,144 (AMF Incorporated) discloses a pipeline pig having a plurality of wheels mounted thereon which are urged into rolling contact with the inner wall of a pipeline. Associated with each wheel is a rotation sensing device having a rotary portion which rotates as the wheel rotates and a stator portion which includes means for producing a signal that indicates rotation of the rotor relative to a reference position on the stator portion.

Canadian Pat. No. 1,017,141 (Shell Canada Limited) also discloses a pipeline pig utilizing one or more counting wheels and apparatus for determining speed of rotation of individual ones of the counting wheels for calculating distance covered by the pig within the pipeline.

Canadian Pat. No. 1,225,734 (Williamson (TD), Inc.) discloses a hammer for physically striking the interior of the pipeline thereby introducing a sound signal on a periodic basis within the pipeline. Alternatively, a step wheel or other mechanical means may be used for generating a periodic sound vibration within the pipeline. A microphone receives the generated vibrations and feeds the received signal to electronic instrumentation where the sound is amplified, electronically modified or analyzed as desired, and the output of the generating means recorded.

Canadian Pat. No. 1,006,692 (AMF Incorporated) discloses a pipeline pig utilizing a plurality of wheels mounted externally thereof for contact with an inner wall of a pipeline to be measured. The array of wheels experiences a difference in distance travelled by each such wheel in the array when traversing a curved section of the pipe, such that by encoding the rotational output of the wheels as a function of axial or shaft position with digital shaft encoders, data is obtained for determining the curvature of the pipe in radians per foot and the location in the pipe of the measured curvature can be identified.

As discussed above, other prior art pigs use gyro or accelerometer based orientation measurement systems for determining curvature and location within a pipeline.

For example, U.K. Patent Application GB 2088554 (PLS Pipeline Service U.K.) discloses a pipeline pig for measuring the distance travelled through a pipeline by means of either a magnetic or gyro compass, or an accelerometer for measuring changes of direction of the pipeline.

Canadian Pat. No. 1,199,169 (Litton Systems, Inc.) discloses a pipeline pig having an inertial reference system, roll control apparatus for providing a stable reference for the inertial system, and a mechanical pig-to-pipe attitude detector in the form of spring loaded arms for contacting the interior wall of the pipeline to provide continuous indications of relative orientation of the pig with respect to the pig interior. All of the data received by the sensors within the pig is recorded by means of an onboard recorder.

U.S. Pat. No. 4,677,865 (Lehmann) discloses a pipeline pig for travelling through a pipeline supported on and moved by a plurality of runners. Apparatus is provided for changing the angular position of the runners in order to avoid obstructions within the pipe wall. A gyro system is used for measuring angular position of the pig within the pipeline. Position in the axial direction is determined by means of measuring the length of a traction rope trail behind the pig using a radioactive position emi or displacement transducer.

Canadian Pat. No. 1,166,844 (Sunstrand Data Control Inc.) discloses borehole survey apparatus utilizing accelerometers and probe joint measurement. The apparatus is in the form of a pig having flexible joined assemblies for mounting a tri-axial accelerometer package and cooperating centralizer mechanisms for retaining probe sections of the accelerometer in the centre of the borehole casings for improving the accuracy of the signals generated by the accelerometers. As an alternative, the apparatus contemplates use of an angular read-out mechanism in the form of a square flexible bar secured to each probe section for supporting a semi-conductor strain gauge for detecting small angular deflections on the pipeline wall.

Other pipeline pigs use magnetic detectors or a combination of magnetic and gyro or accelerometerbased detection to determine pipeline characteristics.

U.S. Pat. No. 4,105,972 (British Gas Corporation) discloses a pipeline pig for detecting defects in the pipeline wall by means of a plurality of spring loaded pivotally connected linked plates which are fully supported for encircling the body of the pig vehicle. The outermost plate carries flux sensing devices which are urged by springs resiliently to engage the inner surface of the pipeline wal.

U.S. Pat. No. 4,292,588 (Schlumberger Technology Corporation) discloses an electromagnetic thickness tool for measuring the wall thickness of a ferromagnetic casing by measuring the amplitude and phase of the time rate of change of flux passing through the casing wall as a function of depth within the casing.

U.S. Pat. No. 4,628,260 (Kimoto et al) teaches an eddy current defect detecting system for metal tubes comprising a detector including test coils movable axially through the metal tube for detecting as an impedance variation a fluctuation in eddy current produced due to a defect present in the metal tube.

U.S. Pat. No. 4,717,875 (Atlantic Richfield Company) discloses a pipeline pig having an onboard instrument package, including accelerometers and a longitudinal position measuring device comprising a magnetometer for counting the girth welds or other known magnetic anomalies along the section of pipeline to be measured.

Each of the above discussed prior art patents teach use of one or both of inertial measurement systems (i.e. accelerometers and gyro systems) and mechanical velocity or location detection apparatus (e.g. wheels mounted to the exterior of the pig in contact with the pipeline wall, or mechanical sound vibration hammers or stepped wheels, etc.) for measuring profile characteristics of a subterranean pipeline, or magneticbased systems for detecting defective pipelines.

The prior art approaches utilizing three dimensional position and curvature determination result in a unique (i.e. non-redundant) solution. Thus, it is extremely difficult utilizing such prior art systems to qualify data integrity with any statistical confidence. Furthermore, inertial based systems (i.e. accelerometers and gyroscopes) when used in isolation, require information first to complete, and thereafter to maintain proper alignment. Otherwise, such systems are prone to generating erroneous acceleration or orientation information in which the errors propagate throughout subsequent measurement processing and interpretation.

The prior art systems which disclose use of mechanical components such as arms, wheels, gears, servo loops for performing velocity or location detection within the pipeline suffer disadvantages which are germane to all mechanical moving parts, namely, the use of such mechanical components in pipeline pigs eventually results in failure due to fatigue and stress due to the harsh operating environment within subterranean pipelines. This problem is exacerbated when the pig must remain within the pipeline for long duration runs.

In addition, all of the above described prior art patents utilize one of either onboard battery packs for powering the measurement systems and sensors, or power cables which extend to the pig through the pipeline from a surface power generator. Cable operated pig powering systems are cumbersome to use and impose constraints on the distance the pig is capable of travelling within the pipeline. On the other hand, battery powered pigs are operable for only short to medium length runs, until battery power is depleted.

SUMMARY OF THE INVENTION

According to the present invention, an integrated pipeline pig monitoring system is provided in which a primary measurement system (strapdown inertial system) comprising inertial sensors such as accelerometers and gyroscopes, is used in combination with a secondary measurement system, for generating a non-unique position and curvature solution to pipeline analysis. The secondary system includes one or more of Doppler sonar velocity sensors, pig-to-pipe attitude sonar caliper sensors, acoustic weld detectors, odometer wheel etc., for calibrating and refining the data generated by the inertial primary measurement system.

For example, data from the pig-to-pipe attitude sensors may be processed in conjunction with the accelerometer derived displacement data to derive a curvature estimate, or alternatively may be processed in conjunction with the gyro based orientation data to derive the estimate of curvature. Accordingly, a redundant solution to curvature is from which a "best fit" estimate may be obtained.

As discussed above, primary inertial based data is often subject to orientation errors such that, when used to generate a unique solution of curvature or other characteristics, the solution incorporates the measurement error, and cannot be corrected by postprocessing. In effect, the secondary measurement system of the present invention generates a supplemental source of raw data which can be used to check and correct the primary derived data, as well as to provide a bounding mechanism for the information generated by the strapped-down gyro system, thereby limiting any propagation of errors as occurs in prior art gyroscope based inertial measurement systems.

The pig-to-pipe attitude sensor also provides an indication of ovality and ripple detection in the pipeline. These are important additional considerations which have not been addressed by priorart systems.

Furthermore, since the secondary measurement system is based on sonic information, the prior art disadvantages of mechanical equipment failure are entirely overcome.

According to the present invention, all of the primary and secondary measurement data is recorded as raw data for later retrieval and post processing. The primary and secondary measurement data can then be compared and any propagating errors may be recognized and filtered accordingly. This approach simplifies hardware and software design characteristics of the inventive pipeline pig as compared with the prior art since there is a very small computing load in the pig itself and the onboard software operates primarily as a data management and communications system According to another feature of the present invention, an onboard power generator is provided for generating DC voltage for powering the primary and secondary measurement systems. Thus in contrast with prior art battery powered or remote powered pipeline pigs, the pig of the present invention is capable of remaining within the pipeline for extended duration runs without replacing batteries or requiring cumbersome power cable connection.

In accordance with an aspect of the present invention, there is provided a pipeline monitoring system, comprising:

carrier means adapted for travelling through a pipeline;

a strapdown inertial system mounted within said carrier means for measuring dynamic characteristics of said carrier means within said pipeline relative to an inertial frame of reference, and in response generating first predetermined digital signals representative of said characteristics;

redundant sensor means mounted within said carrier means for redundant measuring of one or more of said dynamic characteristics relative to said pipeline, and in response generating further predetermined digital signals representative thereof; and recorder means mounted within said carrier means for receiving and recording said first and further predetermined digital signals for subsequent retrieval, whereby upon retrieval said first and further predetermined digital signals yield a nonunique solution of profile and structural characteristics of said pipeline.

In accordance with a further aspect of the present invention, there is provided a pipeline monitoring system, comprising:

carrier means adapted for travelling through a pipeline;

a plurality of pig rubbers mounted on said carrier means for receiving flow of fluid or gas within said pipeline and in response propelling said carrier means through said pipeline;

a power generating unit disposed within said carrier means for receiving and diverting said flow of fluid, gas or products and in response generating a primary DC operating voltage; a battery storage unit disposed within said carrier means for generating a backup DC operating voltage in the absence of said primary DC operating voltage, said battery storage unit including recharge means for receiving said primary DC operating voltage and in response maintaining said backup DC operating voltage at a predetermined level;

a strapdown inertial system disposed within said carrier means for measuring acceleration and angular orientation of said carrier means relative to an inertial frame of reference, and in response generating a series of primary digital signals representative of said acceleration and angular orientation;

a velocity measurement system disposed in said said carrier means for measuring velocity of said carrier means relative to said pipeline and in response generating first series of secondary digital signals representative of said velocity;

an attitude measurement system disposed in said carrier means for measuring angular orientation of said carrier means relative to said pipeline and in response generating a second series of secondary digital signals representative of said angular orientation of said carrier means relative to said pipeline;

a location measurement system disposed in said carrier means for measuring location of said carrier means relative to said pipeline and in response generating a third series of secondary digital signals representative of said location; and a recorder system disposed said carrier means for receiving and storing said series of primary digital signals and said first, second and third series of secondary digital signals, whereby said first, second third series of secondary digital signals provide independent redundant verification of said acceleration and angular orientation measured by said inertial system.

INTRODUCTION TO THE DRAWINGS

A preferred embodiment of the present invention will be described in greater detail below in conjunction with the following drawings, in which.

DETAILED DESCRIPTION OF THE PREFERRED

Figure 1:
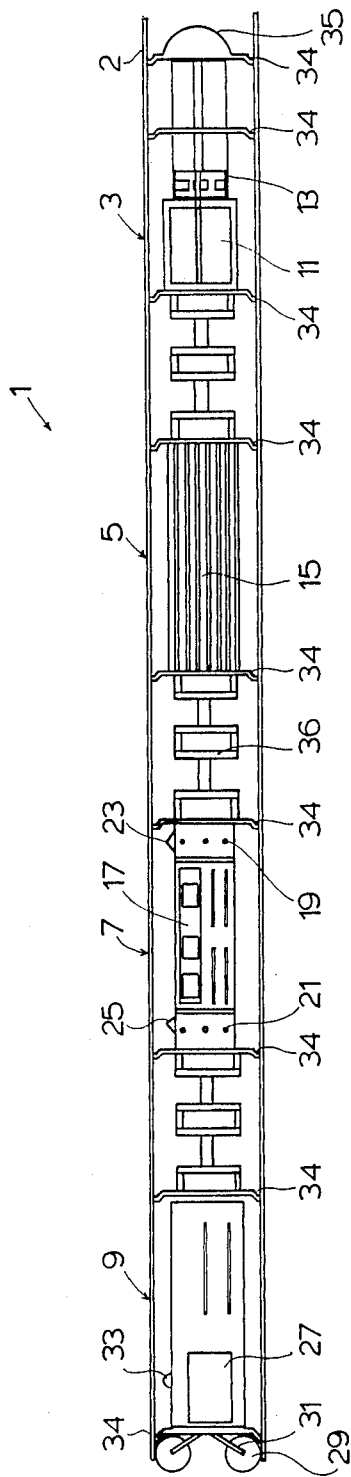
FIG. 1 is a schematic cross-sectional view of a pipeline pig in accordance with the present invention.

Turning to FIG. 1, a pipeline monitoring system is shown in accordance with the present invention in the form of a pig 1 for travelling through an oil or gas or products pipeline 2 of predetermined diameter. The pig comprises a plurality of tubular carriers 3, 5, 7 and 9. The first carrier 3 houses a power generator comprising an alternator 11 and turbine 13 as discussed in greater detail below with reference FIG. 4. The second carrier 5 houses a battery pack 15, also discussed below with reference to FIG. 4. The third tubular carrier 7 supports the primary inertial measurement system 17; a caliper sonar unit including fore and aft sonar transducers 19 and 21, respectively; as well as a Doppler sonar unit including fore and aft Doppler sonar transducers 23 and 25, respectively. The fourth and last carrier 9 houses a digital recorder 27, an optional odometer unit including odometer wheels 29 supported by spring loaded arms 31, and a tuned microphone 33 for detecting girth welds within the pipeline 2.

Each of the carrier units 3–9 includes two or more pig rubbers 34, which are well known cup-shaped flanges extending circumferentiall around the tubular carriers and which are adapted to receive a flow of fluid such as oil or gas within the pipeline 2 and in response to propel the pig 1 therethrough. In addition, the foremost carrier unit 3 optionally includes a tapered nose cone 35 for effective introduction of the pig into check valves and other pipeline fittings. Successive ones of the carrier units 3–9 are interconnected via constant velocity universal joints 36 in order to form an articulated structure capable of adapting to various curvature profiles within the pipeline 2.

The carriers 3, 5, 7 and 9 are preferably fabricated from stainless steel tubing of appropriate diameter relative to pipeline 2. End plates of the carriers are sealed via O-rings to avoid leakage within the pipeline 2. The carriers are preferably designed to a minimum 1500 PSI pressure ratings, yielding sufficient safety margins to operate with confidence in either gas, oil or products pipelines. Standard urethane cup shaped pig rubbers 34 are only used at the forward end of the tool and serve as a propulsion seal. All remaining rubbers are either specially designed drag rubbers or reduced vibration suspension rubbers.

Although the embodiment shown utilizes four separate carrier units for housing the various sensors, as well as the power generation and recording apparatus, it is contemplated that for larger diameter pipelines, fewer articulated carrier units of larger diameter may be substituted for housing the various components. As an example, for a 24", 36" or 48" pipeline, it is possible that all of the measurement, power generation and recording apparatus may be disposed within a single carrier unit or a pair of articulated units.

Figure 2:
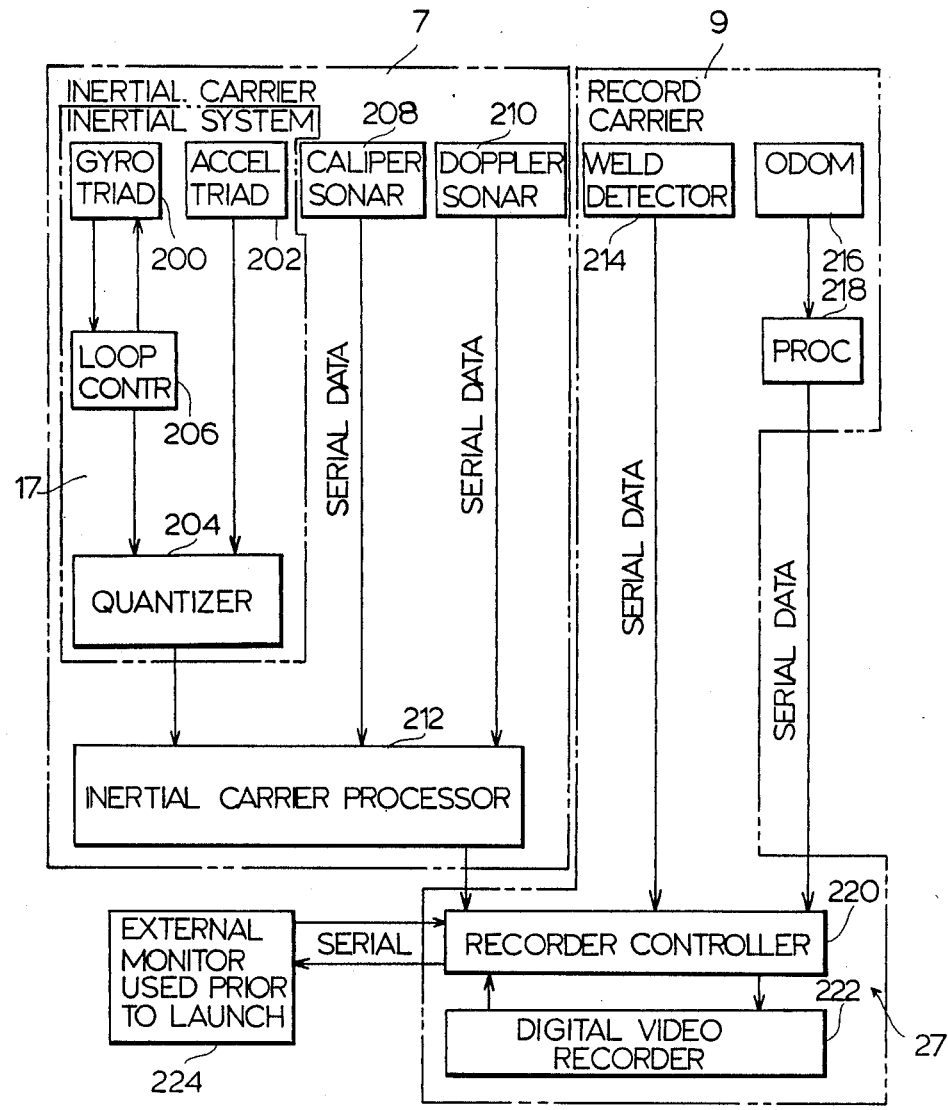
FIG. 2 is a block diagram showing the overall system structure of the pipeline pig of FIG. 1.

Turning to FIG. 2, a block diagram representation of the primary inertial and secondary redundant measurement systems is shown along with the recorder 27 within respective carrier units 7 and 9.

In particular, the strapdown inertial system 17 is shown comprising of a gyro triad 200 for measuring angular orientation of the pig 1 in three axes with reference to an inertial reference frame, and an accelerometer triad 202 for measuring acceleration forces along the three axes. The measured orientation and acceleration data are transmitted in analog format to a quantizer 204 for conversion to digital format. A loop control unit 206 is included for nulling the gyro triad 200 responsive to rotation thereof, as discussed in greater detail below.

The accelerometer triad 202 is capable of detecting small radius of curvatures (1–20 meters) whereas the gyro triad 200 is useful for detecting large radius of curvatures, such that the combined gyro triad 200 and accelerometer triad 202 provides an accurate measurement of curvature according to both small and large radius scenarios.

The accelerometer triad 202 provides data for alignment of the gyro triad 200 when coupled with the Doppler sonar data, thereby compensating for the earth's angular velocity and at the same time providing short and long term gyro drift biases for offsetting any masking of curvature data within the gyro triad 200.

Thus, the gyro triad 200 and accelerometer triad 202 operate as complementary sensors providing alignment (static and dynamic) as well as orientation verification, and generating pipeline curvature and orientation of curvature data to the recorder 27 by means of inertial carrier processor 212.

According to the preferred embodiment, the inertial measurement system 17 is in the form of a strap down system such as the Honeywell H778 strapdown inertial package. Several other systems are available from inertial system manufacturers such as Litton, Condor and SAGEM. This package is an integrated unit, designed primarily for military applications (e.g. missiles, weapons pointing, etc.).

As discussed above, rotation and acceleration data received from the inertial measurement system 17 is converted into computer readable digital form by the quantizer module 204 and is thereafter transmitted to the inertial processor 212. The quantizer 204 measures the change in signal level from epoch to epoch using differential techniques, and conducts measurements over a period of time rather than at discrete intervals as is provided by normal analog to digital converters. Thus, the quantizer 204 may be thought of as a very accurate differential analog to digital converter with accuracies in the order of a few parts per million. Logic circuitry (not shown) is preferably included in the quantizer 204 in order to avoid round-off errors and to correct small excursions above the natural data rate of the device.

Output from quantizer 204 to the inertial processor 212 is in the form of digital rotation rates and changes in velocity. The rotation data is output through individual 8-bit parallel (one for each gyro axis) at a rate of sixteen times per second. The accelerometer data is output either similar scheme or via three tri-state pulse trains (one for each axis). In addition to the differential accelerometer outputs, analog voltage levels representative of the gravitational forces registered by each accelerometer are also generated. These signals are not sufficiently accurate to be used as inertial data inputs but do provide an auxiliary means for monitoring the pig attitude.

The inertial control loop 206 is the means by which rotation is sensed on a gyro axis. As the gyro axis is rotated, the spinning wheel thereof will move slightly in its axle. An electronic sensor is used to measure this movement. The control loop 206 attempts to keep the spinning wheel at a null position at all times by electrically torquing or moving the wheel back into the null position. The amount of current expended by the loop control 206 provides a measure of the rotational rate of the gyro axis, a digital representation of which is transmitted by the quantizer 204 to the computer processor 212 as a rotational rate. The gyro type can also be varied to include RLG (ring laser gyro) and convection gyros as required.

In contrast with prior art inertial based systems, the system of the present invention includes no apparatus for attempting to maintain the gyro triad 200 or the pig 1 at a constant attitude within the pipeline 2. Instead, the current attitude of pig 1 with respect to inertial space is computed using digital processing techniques and then rectified to the pipline using a caliper sonar 208 in conjunction with gyro rates, accelerometer rates, and Doppler velocity provided by a sonar unit 210.

The caliper sonar unit 208 transmits and receives and digitizes analog signals from the transducers 19 and 21 (FIG. 1) and in response generates a serial data signal representative of orientation of the pig 1 within the pipe 2 (referred to herein as "pig-to-pipe attitude"). The Doppler sonar 210 is also included for receiving and digitizing signals from the Doppler sonar transducers 23 and 25 (FIG. 1), and in response generating a further serial data signal representative of the pig velocity within pipeline 2.

The Doppler sonar 210 provides the primary velocity redundancy information according to the system of the present invention. Doppler sonar offers the advantage of having no moving parts and does not require any physical contact with the pipe surface, in contrast with prior art systems. There is therefore little chance of mechanical failure caused by collision with valve flaps and/or debris within the pipeline 2. Since there is no dependence on mechanical contact such as in wheel based odometer systems, the Doppler sonar 10 is characterized by a complete absence of traction induced errors. The estimated repeatable accuracy of sonar 210 is in the order of one part in one thousand. Odometers, on the other hand, have an accuracy of typically one to two percent.

The Doppler sonar 210 functions on the basis that soundwaves reflected from a surface moving in relation to a receiver/transmitter will be frequency shifted according to the velocity difference.

The Doppler shift equation is:

$fd = 2Vfo\cos\theta/Vs$;

where fd represents the frequency shift; V represents the velocity of the reflection point; Vs represents the velocity of sound in the medium of transmission; $\theta$ represents the angle of the sound beam to horizontal; and of represents the frequency of the transmitted ultrasonic beam.

Utilizing the above equation, it is seen that the typical frequency shift on a 10 mHz ultrasonic signal at a velocity of 0.7 meters per second and at an angle of 45°, will be approximately 6.5 kHz.

In order to minimize platform pitch induced errors, the system of the present invention utilizes a dual axis design. In this way, pitch induced error is cancelled between the two transducers.

The Doppler sonar 210 may be implemented in either pulsed or continuous wave fixed angle modes.

The serial data signals output from quantizer 204, caliper sonar unit 208 and Doppler sonar unit 210 are received via inertial carrier processor circuit 212 and multiplexed therein in accordance with a predetermined sequence for further transmission to the recorder 27.

In particular, the inertial processor 212 collects and correlates all serial data received from the primary inertial measurement system 17 as well as the caliper sonar 208 and Doppler sonar 210. The data is assembled in packets for transmission via a serial data link to the recorder 27. Although not shown in detail, the inertial processor comprises an interface for receiving serial data signals from the various sensors, typically in the form of 8-bit parallel input ports or a combination of 8-bit ports and readable up/down counters which are serviced on a 16-Hz interrupt basis; as well as an analog to digital convertor in the form of a multi-channel convertor for monitoring thermal coupled data from the primary inertial measurement unit 17; a CPU; as well as RAM and EPROM memory. A serial input/output port is also provided for communication with the caliper sonar 208 and Doppler sonar 210. Furthermore, a timer apparatus is preferably provided for implementing interrupts and time tagging or stamping of serial data. The processor, RAM, EPROM, serial ports and timers are preferably implemented using a single board computer such as the NEC V40 16-bit microprocessor.

The various devices housed within inertial carrier 7 require a number of different power types including +5 VDC, +/−15 VDC, 400 Hz and 45 kHz AC. Thus, a power supply convertor (not shown) is included for generating all of the required supply voltages from the nominal 28-volt pig power supply.

The record carrier unit 9 incorporates a weld detector 214 for receiving audio signals from the tuned microphone 33 (FIG. 1) and in response detecting the characteristic frequency of contact noise between girth welds and the pig rubbers 34. The audio signals are converted via weld detector 214 into a serial data signal for transmission to recorder 27.

An odometer circuit 216 is optionally included for operating in conjunction with a processor 218 to receive velocity information from associated odometer wheels 29 supported via arms 31 (FIG. 1) and in response generating a further serial data signal.

The additional serial data signals received from weld detector 214 and optional odometer processor 218 are transmitted along with multiplexed serial data signals from inertial carrier processor 212 by a recorder controller 220 forming an operative portion of recorder 27. The recorder controller 220 time stamps and organizes the received serial data signals and controls storage thereof onto a suitable recording medium such as digital video recorder 222.

Prior to launching the pipeline pig 1 within a pipeline 2, preliminary digital control information may be loaded into the recorder controller 220 for controlling operation thereof in accordance with established initial conditions. An external monitor 224 is shown for this purpose. Similarly, upon completion of a run, the serial data stored within recorder 27 is down-loaded for further analysis and post-processing in order to determine precise profile characteristics of the measured pipeline 2.

In operation, the inertial system 17 provides data in the form of orientation of the pig 1 relative to an inertial reference frame, in combination with rectifiable acceleration, velocity and displacement data also relative to an inertial or earth reference frame. However, in order to extract accurate information pertaining to the pipeline characteristics using traditional techniques (i.e. when used in isolation as in prior art systems), the gyro triad 200 must remain in the centre of the pipeline 2. Unfortunately, traditional practical applications of such inertial measurement systems yield erroneous and unpredictable results due to the fact that the inertial measurement system cannot be maintained accurately at the centre of the pipeline 2, as a result of buffeting of the pig 1 etc., as it travels through the pipeline.

Thus, as discussed above, the secondary measurement system is provided including caliper sonar 208, Doppler sonar 210, and weld detector 214, as well as the optional odometer 216, which are used to calibrate and refine the data acquired from the primary measurement system. The data acquired from caliper sonar 208 and Doppler sonar 210 can also be utilized to control the inertial system 17 as well as providing an independent estimate of location in the pipeline 2 when coupled with an as-built survey during post-processing.

Figure 3:
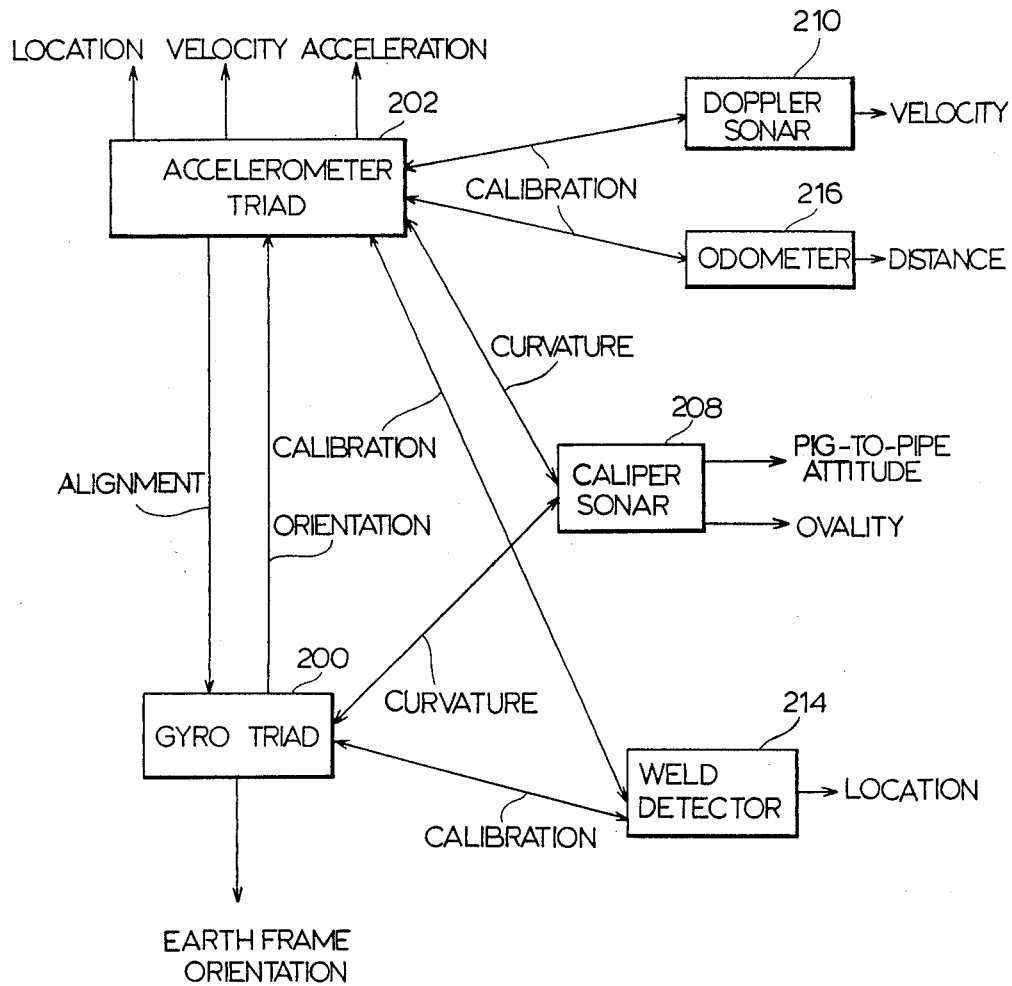
FIG. 3 is a block diagram showing post-processing data source combinations for yielding pipeline characteristics from the pipeline data acquired from the pipeline pig in FIG. 1 and 2.

The data received from the accelerometer triad 202 may be integrated to yield velocity information, and double integrated to yield location information, as shown diagrammatically with reference to the block diagram of FIG. 3. However, without initial or boundary conditions being specified, the derived velocity and location data may result in propagation of considerable error. For example, gravitational force measured by the accelerometer triad 202 may result in a propagating error during integration of the measured acceleration data in the event of small perturbations in the measured angular orientation data via the gyro triad 200.

Thus, in accordance with the present invention, the secondary measurement system is provided for bounding any error growth or propagation resulting from integration of the acceleration data or orientation data provided via the primary inertial measurement system 17, as shown with reference to FIG. 3.

The pig-to-pipe attitude sensor (e.g. caliper sonar 208) provides data which, when coupled to either the accelerometer derived displacement data or to the gyro based orientation data, may yield separate curvature estimates (i.e. redundant non-unique solution).

Furthermore, the caliper sonar 208 may also provide information relating to ovality and ripple detection within the pipeline 2. These are important additional considerations in assessing the pipe condition and are an indirect benefit of utilizing the caliper sonar 208 in accordance with the present invention.

The Doppler sonar 210 and odometer 216 provide velocity sensing which generates boundary conditions for initial calibration and on-going calibration maintenance of the primary inertial measurement system 17. The Doppler sonar 210 is an extremely accurate velocity device (i.e. less than 0.3 cm per second accuracy). The weld detector 214 can be used as both a velocity and displacement calibration tool for the primary inertial measurement system 17, as well as for yielding independent location measurement, resulting in a redundant non-unique solution for location.

As an adjunct to the various non-mechanical velocity and location detection sensors of the present invention, a mechanical odometer 216 may be utilized for data cross-checking purposes. However, it is contemplated that the odometer apparatus may be discarded in the future upon refinement of the aforementioned non-mechanical features.

The odometer 216 comprises a plurality of nylon wheels 29 mounted on arms 31 which are maintained spring loaded against the inner walls the pipeline 2. Wheel rotation is sensed via proximity sensor devices in the arms 31 for detecting rotation of the wheels 29. The processor 218 collects the data from odometer 216 and generates a serial data stream in response thereto, for transmission to the recorder 27. According to the preferred embodiment, the processor 218 is implemented by a single chip Intel 8048 computer.

Moreover, survey information in the form of an as-built plan may be used in post-processing of data recorded by the pig 1 to provide additional data on the pipeline profile which can be further utilized to slew the positional record of data retrieved from the accelerometer triad 202 and weld detector 214. In epoch to epoch measurements, the historical information on weld separation may give a researcher some feedback on the structural integrity of the pipeline by determining the compression or tension forces acting on the pipeline.

Figure 4:
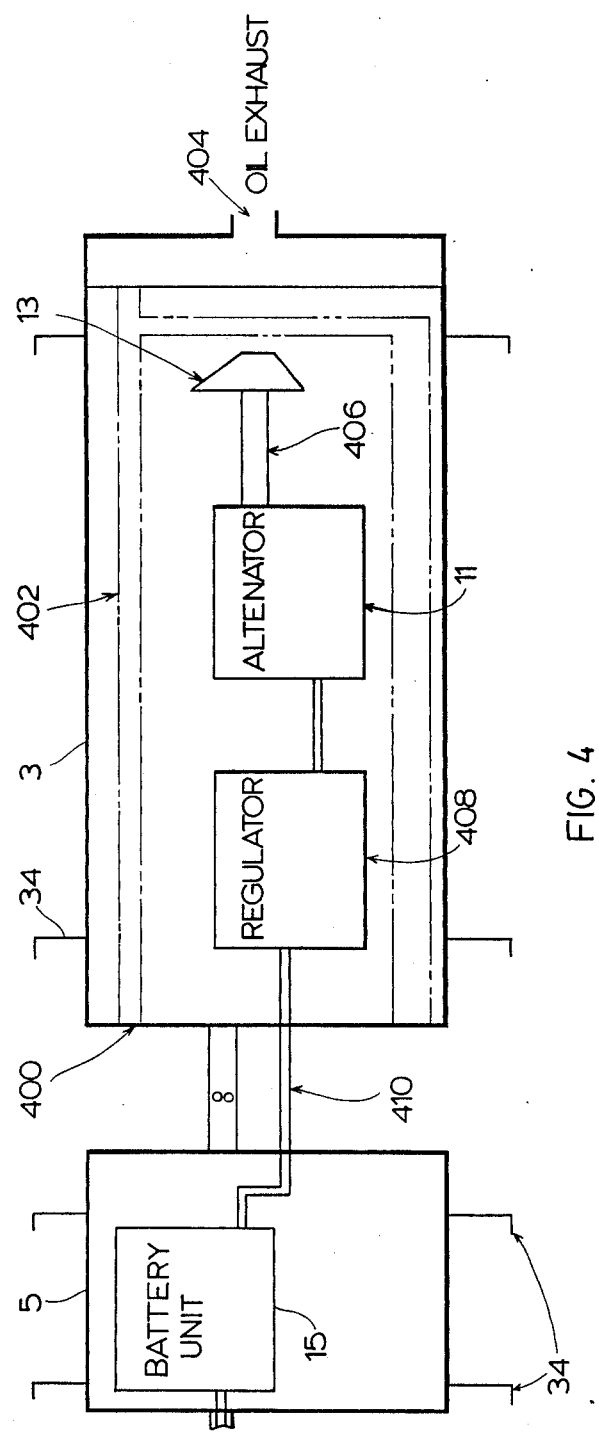
FIG. 4 is a block diagram illustrating a turbine power unit in accordance with the preferred embodiment.

Turning to FIG. 4, a block diagram is shown illustrating an onboard power generator housed within carrier 3, connected to the battery unit 15 housed within carrier 5.

The onboard power generator utilized in the present invention is in the form of a standard Franklin Rotor, with flow reverse. Conceptually, the generator is a miniature version of the type of turbine device used in hydroelectric generators. The basic requirement for power generation is to make the pig 1 travel slower than the average fluid flow within the pipeline 2. In the limit, in the event that the pig 1 is stationary, the theoretical available power would be the equivalent of the flow work, less some losses in the pipeline 2. The maximum power requirements for the primary and secondary measurement systems, including a liberal safety margin of two to three times, is expected to be in the vicinity of 150 watts or 0.2. The power head required to develop 0.2 horsepower (assuming 60% efficiency) is provided by a velocity differential of from 0.1 to 0.4 feet per second a flow head for pump bypass diameters of 0.75 to 1.25 inches.

In addition to the components discussed with reference to FIG. 1, the power generator housed within carrier 3 further comprises an oil inlet 400 and internal pressure vessel 402 for conveying bypassed fluid flow (i.e. oil or gas), and an oil or gas exhaust 404 at the nose cone 35 (FIG. 1). The impeller or turbine 13 is connected to the alternator 11 by means of a pressure balance sealed shaft 406. The alternator 11 is further connected to a regulator 408 for regulating the DC voltage generated by alternator 11 in accordance with well known principles. The regulated DC voltage output from regulator 408 is transmitted to the adjacent battery unit 15 via a connecting power bus 410.

The high power requirements of the inertial measurement system 17 alone (approximately thirty watts) and the typically long duration of measurement runs (e.g. seven days) dictate the use of onboard power generation rather than relying solely on battery storage, as in prior art systems. A primary power calculation has indicated that more than four meters of carrier length would be required to carry enough nicad batteries to power the system of the present invention for seven days. The use of batteries is possible but not attractive from either a financial or logistical standpoint.

The range of viscosities of crude oil makes the use of a small bypass turbine power generator according to the present invention particularly attractive. The turbine 13 derives its power by allowing a small cross-sectional area (0.75 square inches) of oil to bypass the pig rubber seals 34 to drive the turbine 13. Power head is essentially derived from the friction force of the pig rubbers 34 against the inner walls of pipeline 2. In the event that the friction force from the rubbers alone is insufficient to slow the pig 1 and generate power, a force brake system could be embodied.

As discussed, the power transferred to the turbine 13 is accomplished by slowing the pig 1 down in relation to the oil flow. For example, a difference in velocity between the pig and the oil of one-tenth foot per second will result in the flow through a one-square inch bypass 402 of approximately nine feet per second.

The turbine characteristics, shaft 406, and alternator 11 are optimized for the present application such that the relative velocity between the pig 1 and fluid flow may be up to 0.3 feet per second for providing an effective power head through the 0.75 square inch bypass 402 necessary to deliver 100 watts of power.

Screened bypass holes may be installed between the pig rubbers 34 and carriers 5, 7 and 9 for directing the fluid flow to enter inlet 400 of carrier 3. The bypass holes are of sufficiently small sectional area that in the event the rubbers 34 on the drive or turbine section fail, the pig 1 will still move down the pipeline 2 without becoming stuck.

The bypass turbine of the present invention is designed to generate an average of 100 watts of power or more, which is more than twice what the pig 1 requires. This allows a sufficient safety margin to account for inefficiencies in the event that the pig rubber friction is overcome, for example, on a downhill pitch.

The alternator 11 is a specially designed high efficiency generator with an external rotor which makes possible a high packing density in a small diameter casing which is driven off of the turbine 14 by means of shaft 406.

The regulator 408 is designed to allow "soft starting" of the alternator 11 should turbine 13 be in a stalled position. The regulator 408 will enter a soft starting mode by reducing the demand current requirements so that the alternator and turbine are free spinning until a predetermined threshold RPM is achieved. A dummy load is also incorporated within regulator 408 to increase current draw at higher rotational revolutions to thereby limit the flow of fluid through the turbine 13.

The alternator output is used to charge a sealed lead acid battery pack 15 of preferably 140 cells at 2.5 AH for a total 350 AH capacity. The battery pack 15 also provides a filtering effect on the pig power supply lines (28 volts DC) and serves to hold the power at a predetermined threshold through periods when the turbine is incapable of generating sufficient power, such as on a steep downhill grade.

In order to translate the inertially derived coordinates to pipe centre coordinates, it is necessary to continuously monitor the distances from the pig 1 to the pipeline 2 at each end of the intertial carrier 7, as discussed above. This measurement process can be thought of as the use of multi-point calipers at each end of the inertial carrier.

Rather than utilize a conventional mechanical caliper system, such as exemplified by the prior art patents, as discussed above with references to FIG. 2, the system of the present invention utilizes an ultrasonic sonar system for measuring pig-to-pipe attitude. The sonar approach results in fewer mechanical and moving parts, thereby overcoming the prior art disadvantages of part failure, fatigue, etc.

Ultrasonic sensing has been used in pipeline applications in the past. For example, non-destructive testing is a prior art procedure by which pipelines are inspected both in the factory or in situ in pipelines using ultrasonic methods. Ultrasonic distance measuring methods are also used in liquid level sensors for both tanks and pipes.

Figure 5:
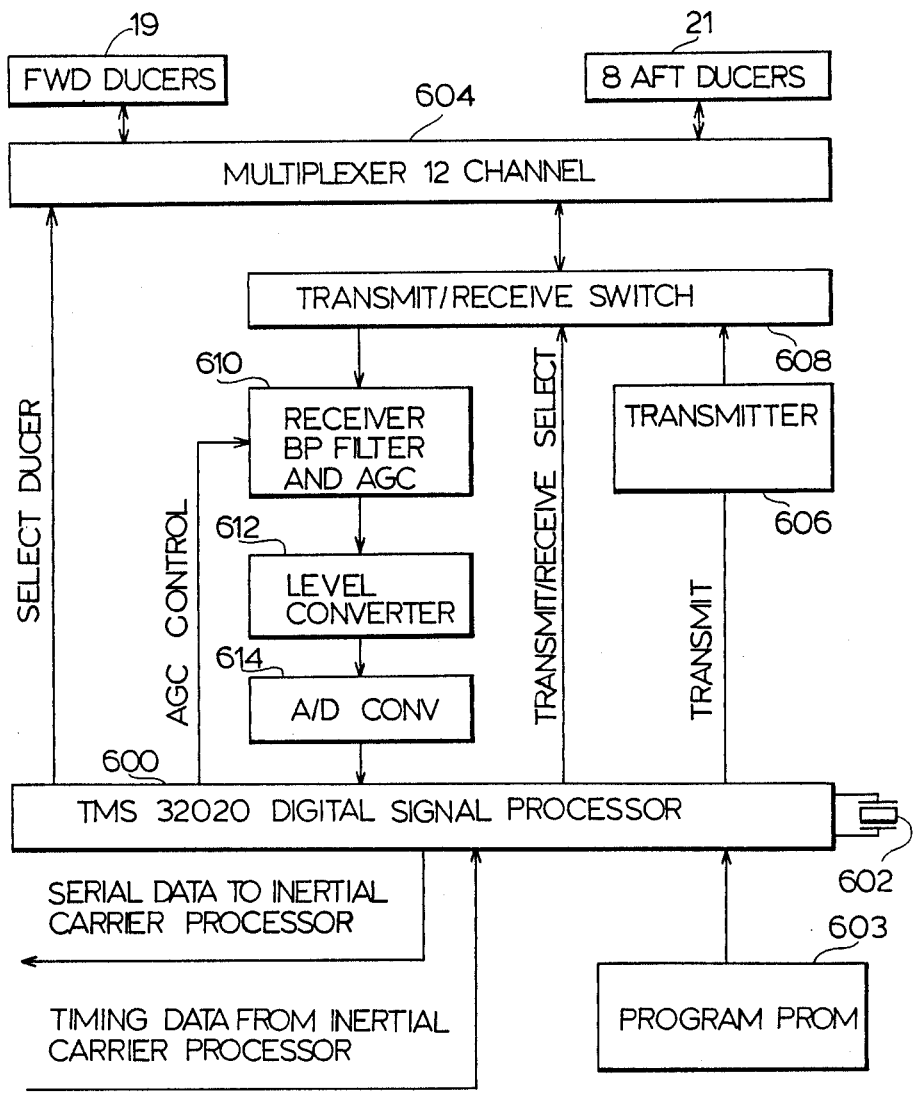
FIG. 5 is a block diagram illustrating a caliper sonar in accordance with the preferred embodiment.

FIG. 5 illustrates a block diagram of the caliper sonar system in accordance with the preferred embodiment. Eight equally spaced ultrasonic transducers 21 are mounted around the circumference of the carrier 7 at the rear thereof. Likewise, four equally spaced ultrasonic transducers 19 are mounted at the front of the carrier 7. The caliper sonar 208 functions by sending a short burst (1-2 microseconds duration) of ultrasonic (e.g. 10 mHz) sonic energy through the transducers 19 and 21 and thereafter measures the time elapsed until the first return echo from the pipe wall is detected. The distance measuring accuracy is in the order of one to two millimeters.

The system operates under the control of a digital signal processor 600 such as a TMS 32020 microprocessor driven by a crystal 602 in a well known manner. The digital signal processor 600 is a high speed (e.g. 5 MIPS) unit with onboard memory, timer and serial port. The microprocessor 600 is capable of making a single measurement in 300 microseconds. A complete scan of the twelve transducers designated by 19 and 21 takes under five milliseconds, resulting in a caliper measurement at both ends of the carrier 7 approximately every four millimeters of travel. This high data rate is not required for the present application and is therefore filtered to a data rate to the inertial carrier processor 212 of approximately 2 Hz, or one measurement every five hundred milliseconds.

In operation, the digital signal processor 600 generates a control signal for selecting a predetermined one of the twelve transducers designated by 19 and 21 using a twelve-channel multiplexer 604. In response to selecting a predetermined transducer, processor 600 generates an enable signal for causing a transmitter 606 to generate the aforementioned ultrasonic signal burst. The ultrasonic signal burst is then applied to the multiplexer 604 by means of a transmit/receive switch 608 under control of the processor 600. Upon completion of generation of the ultrasonic signal burst, microprocessor 600 causes switch 608 to revert to a receive mode such that the ultrasonic echo signal received from the inner wall of pipeline 2 is received via a band pass filter and automatic gain control circuit 610 and thereafter level adjusted via a convertor 612 and digitized via A/D convertor 614.

Processor 600 is also provided with a program PROM 603 for storing operating software for implementing the sonar function, as described in further detail below.

In addition to performing caliper measurement, the sonar 208 can be used to detect girth welds and valves within the pipeline 2. This may be accomplished by mounting the front transducers 21 at an approximately 20° angle in the forward direction of pig 1. Echoes from a girth weld will be somewhat higher in amplitude than echos from a flat pipe. In the event that the majority of transducers detect high signal returns, then it can be assumed that a girth weld is present. The time of detection of the weld is then passed to the inertial processors so that the girth weld location can be correlated to the inertial data.

However, as discussed above, the record carrier 9 preferably houses a weld detector 214 in the form of a tuned microphone. It is known that upon contacting a girth or flash weld within the pipeline 2, the pig rubbers 34 generate a unique frequency sound. Thus, according to the preferred embodiment, the microphone 3 is tuned by means of band pass filtering for detecting the aforementioned unique frequency sound and simultaneously filtering extraneous scratching noises, etc. The detected girth weld contacting sound is digitized and transmitted for time stamping recordal via recorder 27 as discussed above with reference to FIG. 2.

The measurement qualities of the caliper sonar 208 considering pipe boundary conditions (e.g. turbulence eddy effects), laminar flow at the pipewall, and wall deposits have been considered in the instant design.

As discussed above, the return or reflected ultrasonic signal from the inner wall of pipeline 2 is digitized at a relatively high data rate (i.e. 1 to 2 mHz). The digital signal processor 600 examines the digital signal for identifying the first return from the pipewall. Additional extraneous returns may be identified, such as an echo return from particles in the oil, an echo return from waxed deposits, or an echo return from the outer wall.

The echo return from the inner wall will be three to ten times stronger than any of the other extraneous echo returns, and as such will be easily discernable via the software resident in processor 600.

Figure 6:
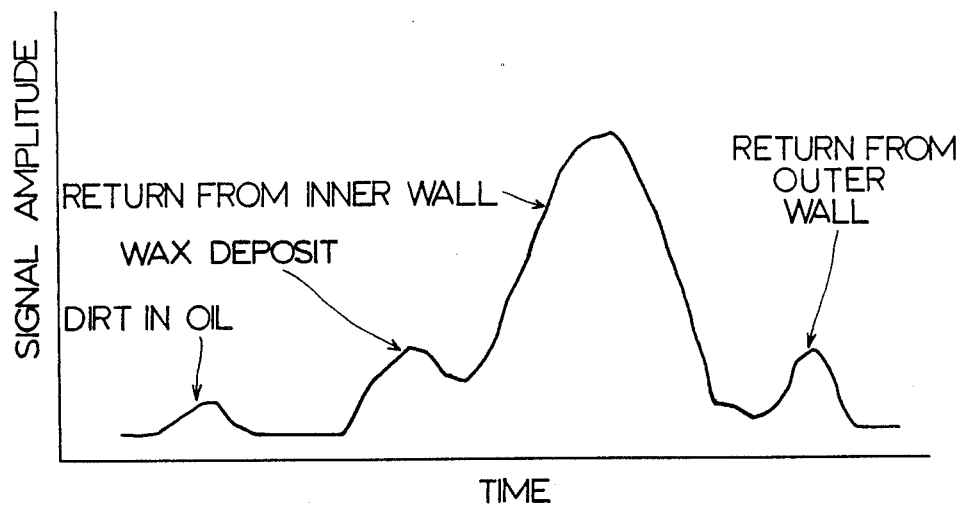
FIG. 6 is a graph illustrating caliper sonar amplitude with respect to time in accordance with the preferred embodiment.

FIG. 6 illustrates the amplitude structure of a typical reflected caliper sonar signal with respect to time.

The caliper sonar system 208 of the present invention does not suffer from problems associated with eddy currents or laminar flows since it has been found that there are very minor changes in acoustic impedance and hence relatively low amplitude return signals as a result of these effects in comparison with the return signal from the inner wall of the pipeline 2.

The aforementioned digitizing rate determines the resolution of the system. For example, a 1 mHz sampling rate digitizes at a resolution of 0.75 millimeters, whereas a sampling rate of 1.5 mHz digitizes at a resolution rate of 0.5 millimeters and a 2 mHz digitizing rate resolves at 0.37 millimeters. According to the successful prototype, the processor 600 is capable of accurately measuring the return sonar echo signal with an error of one to two millimeters, which is more than adequate for the present application. Thus, the system of the present invention is capable of detecting diameter variations in the pipe 2 of three millimeters or less. This translates to one percent for three hundred millimeter pipelines or just over the manufacture's specification.

The mounting of inertial processor 212 within the carrier 7 is preferably effected so as to minimize the possibility of vibration/shock induced failures. Space is preferably provided above and below the processors for inclusion of additional electronic circuitry as required.

Figure 7:
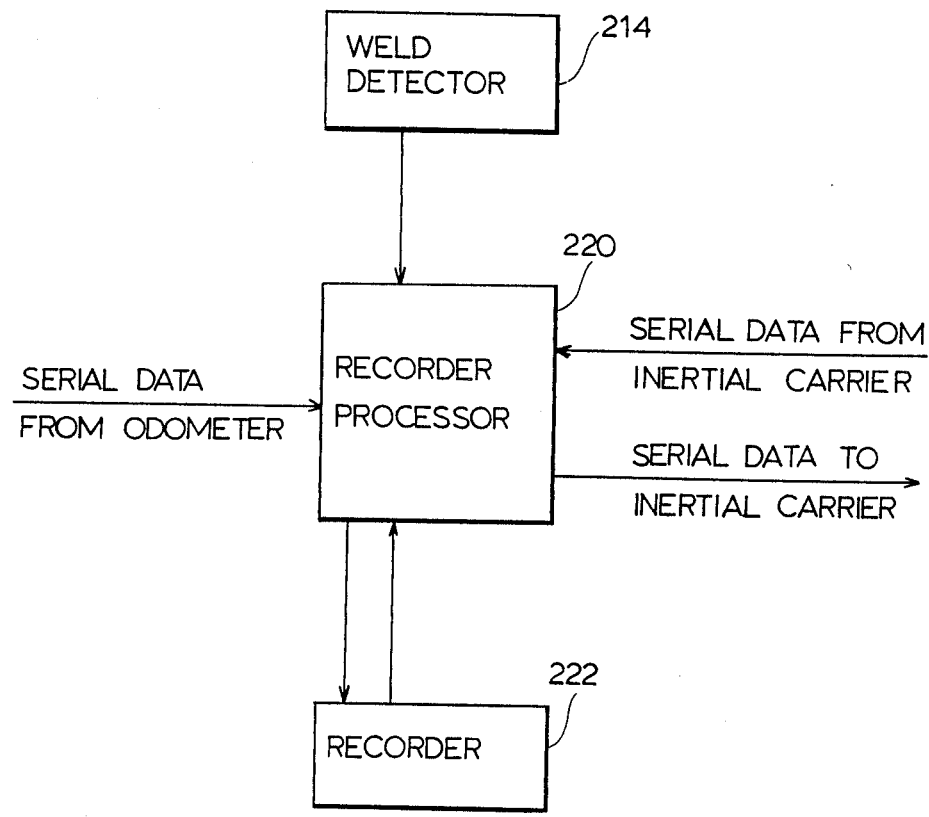
FIG. 7 is a block diagram illustrating a recorder module in accordance with the preferred embodiment.

Turning to FIG. 7, the recorder is shown comprising recorder processor or controller 220 in conjunction with recorder 222 connected to weld detector 214.

According to the preferred embodiment, recorder 222 is in the form of an EXABYTE ™ 8200 digital video recorder. However, alternative recording media are contemplated such as optical discs and magnetic tape cassettes.

The control processor 220 receives data from the Doppler sonar 210, odometer 216 and weld detector 214 as well as the inertial carrier 17 via serial data links (e.g. RS-232). The received data is organized via processor 220 into appropriate file sizes for recording and is sent via a small computer system interface (SCSI) to the recorder unit 222. The recorded data is then verified under control of processor 220 to ensure data integrity.

In addition to the recording function, a bi-directional link to an external computer or terminal may be implemented so that the integrity of the pig 1 can be ascertained without dismantling the unit. An interactive monitoring program is preferably implemented via processor 220 to facilitate this function. Thus, in accordance with this enhancement, the status of the pig 1 may be monitored up until the time of launch.

The large volume of data to be recorded (approximately 500 megabytes) dictates the use of a high density digital recording medium. The preferred EXABYTE ™ 8200 video cassette recorder utilizes eight millimeter video cassettes which are normally found in portable video cameras. The recorder features a "smart" controller which performs error checking, a 256-kilo byte buffer, SCSI interface and a recording capacity of over 2 giga-bytes.

The data recorder 222 is mounted within record carrier 9 by means of vibration resistant shock mounts and thermal insulation in order for the recorder package to retain heat produced by the electronics. The recycling of waste heat produced by the electronics package thus raises the operating temperature of the recorder unit to an acceptable level during cold weather use. These modifications of the recorder, in combination with a good data verification scheme allows the unit to operate reliably in pipeline environments.

Upon extracting the pig 1 from the pipeline 2, the digital data from recorder 27 is down loaded and analyzed for detection of critical pipe curvatures and the location of these critical spots within the pipeline. The detection problem is solved by subdividing the pipeline into easily identifiable sections and scanning the derived data for each section to determine critical curvatures. After all critical characteristics have been detected, the location problem can be solved by tying all sub-divided sections together.

Preferably, a curvature detection algorithm is implemented for analyzing the data output from the inertial system 17 (i.e. orientation and acceleration measurements) and for computing a reference trajectory for the pig 1 within pipeline 2. The sonar velocity is then utilized to limit drift and height errors of the inertial system 17 within predetermined bounds and to improve on the gravity estimation received from the accelerometer triad 202. By making use of the pig to pipe separation sensed by the caliper sonar 208, a pipe centre line trajectory can then be computed. Using the centre line data, critical curvatures in the horizontal or vertical axes can be detected and time tagged from the raw data stored within the recorder 27.

Unique software has been developed for solving the aforementioned curvature detection problem. The major software sub-modules developed for this task include body axes transformation; navigation computation; Kalman filter estimation; curvature detection; and output file and graphics.

All of the above discussed software routines are well known in the art.

In summary, a pipeline pig is provided in accordance with the present invention for deriving accurate angular orientation and acceleration data by means of a primary inertial measurement system 17. The unique data provided by the inertial system 17 is cross referenced and bounded by additional data output from secondary sensors such as caliper sonar 208, Doppler sonar 210, weld detector 214, and an optional odometer 216. Moreover, the sonar and weld detector sensors are non-mechanical, such that prior art problems associated with failure and fatigue of mechanical parts is overcome. Also, the pig according to the present invention utilizes an on-board power generator resulting in the capability of extended, without reliance on stored battery power.

Other modifications and embodiments of the present invention are possible. All such modifications and variations are believed to be within the sphere and scope of the present invention as defined by the claims appended hereto.

We claim:

1. A pipeline monitoring system, comprising:
    (a) carrier means adapted for travelling through a pipeline;
    (b) a strapdown inertial system mounted within said carrier means for measuring dynamic characteristics of said carrier means within said pipeline relative to an inertial frame of reference, and in response generating first predetermined digital signals representative of said characteristics;
    (c) secondary sensor means different from the inertial system mounted within said carrier means for redundant measuring of one or more of said dynamic characteristics relative to said pipeline, and in response generating further predetermined digital signals representative thereof; and
    (d) recorder means mounted within said carrier means for receiving and recording said first and further predetermined digital signals for subsequent retrieval, whereby upon retrieval said first and further predetermined digital signals yield a nonunique solution of profile and structural characteristics of said pipeline.

2. A pipeline monitoring system as defined in claim 1, wherein said inertial system further comprises an accelerometer triad for measuring acceleration forces applied to said carrier means and in response generating digital acceleration signals representative thereof.

3. A pipeline monitoring system as defined in claim 2, wherein said inertial system further comprises a gyro triad for measuring angular orientation of said carrier means relative to said inertial frame of reference and in response generating digital orientation signals representative thereof.

4. A pipeline monitoring system as defined in claim 1, wherein said carrier means comprises one or more stainless steel tubes for housing said inertial system, said secondary sensor means, and said means for receiving and recording, and one or more urethane cup-type pig rubbers disposed at each end of said one or more tubes adapted for receiving fluid flow within said pipeline and in response propelling said carrier means through said pipeline.

5. A pipeline monitoring system as defined in claim 1, wherein said secondary sensor means includes a caliper sonar system comprising a plurality of ultrasonic transducers equally spaced around the circumference of said carrier means for generating a series of ultrasonic signal bursts adapted to reflect off an inner wall of said pipeline, and receiving said signal bursts reflected off said inner wall; and means for measuring elapsed time between generation and reception of said signal bursts and in response generating a digital signal representative of said elapsed time and thereby also representative of attitude orientation of said carrier means to said pipeline.

6. A pipeline monitoring system as defined in claim 1, wherein said secondary sensor means includes a Doppler sonar system comprising a first transducer mounted rearwardly on said carrier means for transmitting an ultrasonic signal at an acute angle to the direction of motion of said carrier means such that said signal is reflected off an inner sidewall of said pipeline and thereby subject to a Doppler frequency shift proportional to velocity of said carrier means within said pipeline, a second transducer mounted forwardly on said carrier means for receiving said signal subject to said Doppler frequency shift, and means for measuring said Doppler frequency shift and in response generating a digital signal representative of said velocity of said carrier means within said pipeline.

7. A pipeline monitoring system as defined in claim 1, wherein said secondary sensor means includes an odometer comprising a pair of wheels mounted rearwardly on said carrier means via respective supporting arms, spring means for urging said pair of wheels against an inside wall of said pipeline, magnet means mounted in each of said pair of wheels, Hall effect detector means mounted in said respective supporting arms for detecting rotation of said magnet means as said carrier means travels through said pipeline and in response generating successive output signals corresponding to successive rotations of said pair of wheels, and means for receiving said output signals and in response generating a digital signal representative of distance travelled by said carrier means within said pipeline.

8. A pipeline monitoring system, comprising:
(a) carrier means adapted for travelling through a pipeline;
(b) a strapdown inertial system mounted within said carrier means for measuring dynamic characteristics of said carrier means within said pipeline relative to an inertial frame of reference, and in response generating first predetermined digital signal representative of said characteristics;
(c) secondary sensor means different from the inertial system mounted within said carrier means for redundant measuring of one or more said dynamic characteristics relative to said pipeline, and in response generating further pre-determined digital signals representative thereof; said secondary sensor means including a weld detector comprising a microphone tuned to a predetermined frequency for detecting a predetermined sound characteristic of pig rubbers of said carrier means contacting girth welds in said pipeline and in response generating a filtered analog signal representative of said sound, and means for receiving said analog signal and in response generating a corresponding digital signal for affecting both velocity and displacement calibration of said strapdown inertial system as well as yielding independent location measurement, thereby affecting said redundant measuring of said one or more dynamic characteristics; and
(d) recorder means mounted within said carrier means for receiving and recording said first and further predetermined digital signals for subsequent retrieval, whereby upon retrieval said first and further predetermined digital signals yield a non-unique solution of profile and structural characteristics of said pipeline.

9. A pipeline monitoring system as defined in claim 1, further comprising means mounted within said carrier means for generating onboard power for operating said inertial system, said redundant means, and said means for receiving and recording based upon the flow of fluid through the monitoring system.

10. A pipeline monitoring system as defined in claim 1, further including an onboard power generator mounted within said carrier means, said generator comprising means for bypassing fluid flow within said pipeline to within said carrier means, a turbine within said carrier means for receiving said fluid flow and in response driving an alternator connected to said turbine, said alternator being adapted to generate DC power in response to being driven via said turbine.

11. A pipeline monitoring system, comprising:
(a) carrier means adapted for travelling through a pipeline;
(b) a plurality of pig rubbers mounted on said carrier means for receiving a flow of fluid within said pipeline and in response propelling said carrier means through said pipeline;
(c) a power generating unit disposed within said carrier means for receiving and diverting said flow of fluid and in response generating a primary DC operating voltage;
(d) a battery storage unit disposed within said carrier means for generating a backup DC operating voltage in the absence of said primary DC operating voltage, said battery storage unit including recharge means for receiving said primary DC operating voltage and in response maintaining said backup DC operating voltage at a predetermined level;
(e) a strapdown inertial system disposed within said carrier means for measuring acceleration and angular orientation of said carrier means relative to an inertial frame of reference, and in response generating a series of primary digital signals representative of said acceleration and angular orientation;
(f) a velocity measurement system disposed in said carrier means for measuring velocity of said carrier means relative to said pipeline and in response generating a first series of secondary digital signals representative of said velocity;
(g) an attitude measurement system disposed in said carrier means for measuring angular orientation of said carrier means relative to said pipeline and in response generating a second series of secondary digital signals representative of said angular of said carrier means relative to said pipeline;
(h) a location measurement system disposed in said carrier means for measuring location of said carrier means relative to said pipeline and in response generating a third series of secondary digital signals representative of said location; and (i) a recorder system disposed in said carrier means for receiving and storing said series of primary digital signals and said first, second and third series of secondary digital signals, whereby said first, second and third series of secondary digital signals provide independent redundant verification of said acceleration and angular orientation measured by said inertial system.

12. A pipeline monitoring system as defined in claim 11, wherein said power generating unit further comprises an alternator, an impeller for receiving said flow of fluid and in response driving said alternator whereby said alternator generates said primary DC operating voltage, and a regulator for regulating said primary DC operating voltage.

13. A pipeline monitoring system as defined in claim 11, wherein said battery storage unit comprises a sealed lead acid battery pack having a capacity of from approximately 20 AH to 30 AH.

14. A pipeline monitoring system as defined in claim 11, wherein said inertial system further comprises an accelerometer triad for measuring acceleration forces exerted on said carrier means in three axes; a gyro triad for measuring said angular orientation of said carrier means in three axes.

15. A pipeline monitoring system as defined in claim 11, wherein said velocity measurement system further comprises first Doppler sonar transducer for directing an ultrasonic signal from an outer aft surface of said carrier means at a predetermined angle toward an inner wall of said pipeline, said ultrasonic signal being directed so as to reflect off said inner wall toward an outer forward surface of said carrier means; a second Doppler transducer mounted to said carrier means at said outer forward surface for receiving said ultrasonic signal, and means for detecting Doppler frequency shift of said ultrasonic signal received by said second Doppler transducer and in response generating said first series of secondary digital signals.

16. A pipeline monitoring system as defined in claim 11, wherein said attitude measurement system further comprises a first plurality of ultrasonic transducers mounted rearwardly of said carrier means for directing a plurality of ultrasonic signals radially therefrom, said ultrasonic signals being directed so as to reflect off an inner wall of said pipeline, said first plurality of ultrasonic transducers being adapted to receive said ultrasonic signals reflected off said inner and in response generate a first analog signal representative of distance from said rearwardly mounted transducers to said inner wall; a second plurality of ultrasonic transducers mounted forwardly of said carrier means for directing an additional plurality of ultrasonic signals radially therefrom, said ultrasonic signals being directed so as to reflect off said inner wall, said second plurality of transducers being adapted to receive said additional plurality of ultrasonic signals reflected off said inner wall and in response generate a second analog signal representative of distance from said forwardly mounted second plurality of transducers to said inner wall, and processor means for receiving said first and second analog signals and in response generating said second series of secondary digital signals.

17. A pipeline monitoring system as defined in claim 11, wherein said location measurement system further comprises a tuned microphone circuit and associated processor for detecting a predetermined sound characteristic of said pig rubbers contacting girth welds in said pipeline, and in response generating said third series of secondary digital signals.

18. A pipeline monitoring system as defined in claim 11, wherein said recorder system further comprises a digital video recorder.

19. A pipeline monitoring system as defined in claim 11, further comprising a pair of odometer wheels mounted rearwardly of said carrier means and means detecting rotation of said wheels and in response generating a further digital signal representative of velocity and distance travelled by said carrier means in said pipeline.

20. A pipeline monitoring system as defined in claim 11, wherein said carrier means further comprises a plurality of series connected tubular carriers adapted for travelling through said pipeline, said tubular carriers being connected via respective universal couplings.

* * * * *

UNITED STATES PATENT AND TRADEMARK OFFICE
CERTIFICATE OF CORRECTION

PATENT NO. : 4,945,775

DATED : August 7, 1990

INVENTOR(S) : John R. Adams et al.

It is certified that error appears in the above-identified patent and that said Letters Patent is hereby corrected as shown below:

Column 2, line 42, "emi" should be --emitter--.

Column 2, line 59, "accelerometerbased" should be --accelerometer-based--.

Column 2, line 68, "wal" should be --wall--.

Column 3, line 27, "magneticbased" should be --magnetic-based--.

Column 4, line 31, "priorart" should be --prior art--.

Column 5, line 40, after "generating" insert --a--.

Column 5, line 53, after "disposed" insert --in--.

Column 5, line 58, after "second" insert --and--.

Column 6, line 6, "FIG." should be --FIGS.--.

Column 6, line 17, after "PREFERRED" insert --EMBODIMENT--.

Column 6, line 40, "circumferentiall" should be --circumferentially-.

Column 7, line 40, after "Honeywell" insert --model--.

UNITED STATES PATENT AND TRADEMARK OFFICE
CERTIFICATE OF CORRECTION

PATENT NO. : 4,945,775

DATED : August 7, 1990

INVENTOR(S) : John R. Adams et al.

It is certified that error appears in the above-identified patent and that said Letters Patent is hereby corrected as shown below:

Column 8, line 64, "of" (2nd) should be --fo--.

Column 11, line 12, after "walls" insert --of--.

Column 11, line 47, after "0.2" insert --horsepower--.

Signed and Sealed this

Thirty-first Day of March, 1992

Attest:

HARRY F. MANBECK, JR.

*Attesting Officer*      *Commissioner of Patents and Trademarks*

REEXAMINATION CERTIFICATE (4068th)

United States Patent
Adams et al.

[11] B1 4,945,775
[45] Certificate Issued May 2, 2000

[54] INERTIAL BASED PIPELINE MONITORING SYSTEM

[75] Inventors: John R. Adams; Patrick S. Price; Jim W. Smith, all of Calgary, Canada

[73] Assignee: Nowsco Well Service Ltd, Calgary, Canada

Reexamination Request:
No. 90/005,355, May 11, 1999

Reexamination Certificate for:
Patent No.: 4,945,775
Issued: Aug. 7, 1990
Appl. No.: 07/362,504
Filed: Jun. 7, 1989

Certificate of Correction issued Mar. 31, 1992.

[30] Foreign Application Priority Data

Dec. 30, 1988 [CA] Canada ................................. 587332

[51] Int. Cl.[7] ........................................... G01C 9/06
[52] U.S. Cl. .............................................. 73/865.8
[58] Field of Search .................. 73/623, 865.8, 73/866.5, 865.9

[56] References Cited

U.S. PATENT DOCUMENTS

4,747,317 5/1988 Lara ........................................ 73/865.8

FOREIGN PATENT DOCUMENTS

2088554 6/1982 United Kingdom .
2130721 6/1984 United Kingdom .

*Primary Examiner*—Robert Raevis

[57] ABSTRACT

A pipeline monitoring system for determining profile, ovality and displacement of oil, gas and products pipelines. The system comprises one or more pig carriers housing a plurality of sensors including a strapdown inertial measurement system, a secondary sonar measurement system, digital recorder, weld detector and odometer. The inertial measurement system detects primary acceleration and orientation data of the monitoring system within a pipeline and the secondary system generates redundant data for verifying the acceleration orientation information provided by the inertial system. The digital recorder records all of the information generated by the various measurement systems and sensors for post ash processing analysis to determine the aforementioned features of profile, ovality and displacement of pipelines.

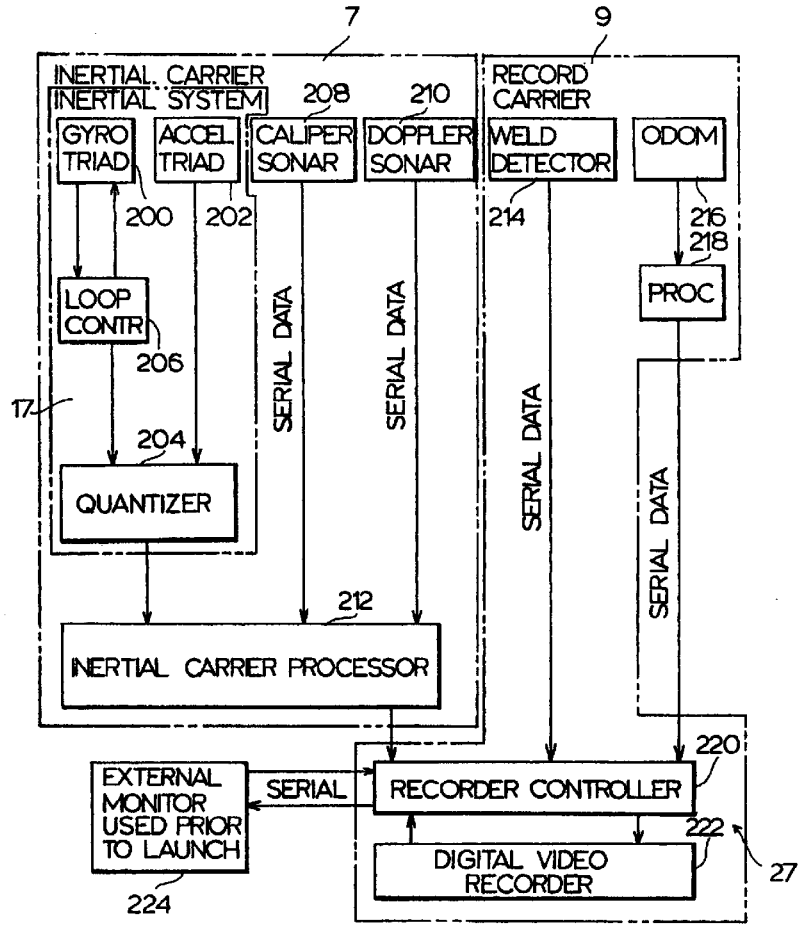

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–20 is confirmed.

\* \* \* \* \*